Nov. 1, 1960 O. O. DUNHAM Plant Pat. 1,979
CHRYSANTHEMUM PLANT
Filed July 27, 1959
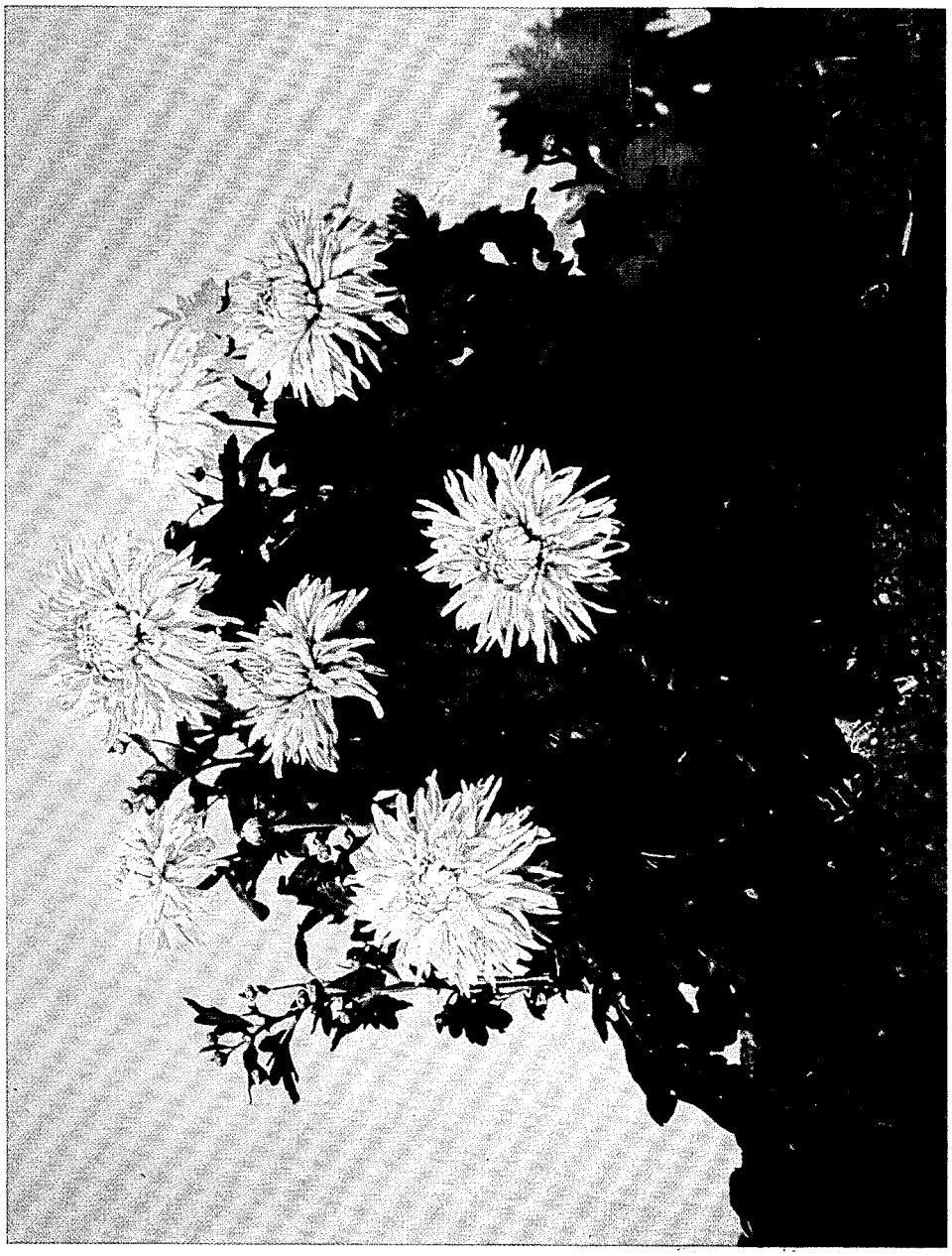
Inventor
O. O. Dunham
by
Robb & Robb
attorneys United States Patent Office Plant Pat. 1,979
Patented Nov. 1, 1960

1,979

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,942

1 Claim. (Cl. 47—60)

My present invention comprises a new and distinct variety of chrysanthemum plant which is the result of cross breeding the variety "Cupid" (unpatented), a variety of my own introduction, and the unpatented variety which I have designated "No. 5350."

The object of my invention has been to produce a new variety of chrysanthemum of the *indicum* type, which has a different and improved color over the parents, with an improved reflex type of flower as well as foliage and plant habit.

This present new variety has resulted from a program of careful selection and cross-breeding which generally speaking has involved so-called American garden chrysanthemums and English early chrysanthemums. The program has been primarily concerned with taking advantage of the most favorable features of both of the basic types, the early flowering date of both and the continuous flowering feature of the English early chrysanthemum, as contrasted with the short flowering period of the American garden chrysanthemum.

The result of the specific hybridization previously mentioned has been to produce my present new and distinct variety of chrysanthemum plant characterized by the pale orange yellow center, pale pink general tonality, improved reflexed type bloom, the very double arrangement of its petals, the earlier, continuous, long blooming period, its more vigorous, compact plant habit and larger, more abundant foliage.

More specifically, the blooms of my new variety are of a generally pale pink color with pale orange yellow center (Nickerson Color Fan published by Munsell Color Company). As grown in the vicinity of Niles, Michigan, under uniform culture, plants of my new variety are of medium height.

While the parents of my new variety are both generally speaking, of the pale pink color, and therefore this characteristic is present in the new variety, the pale orange yellow center is not found in either of the parents, and my new variety differs from both of its parents and some other known varieties in many other respects.

In comparing the blooms of my new variety with the blooms of the parents, it is noted that neither is very reflexed in contrast and further that the parent "No. 5350" is of incurved form, in contrast to the new variety which is reflexed extensively. The petal arrangement of my new variety is very double and the stamens are small and few in number.

Under conditions of culture in the region of Niles, Michigan, the blooms of the pollen parent "Cupid" begin to appear in early October and the blooms of the seed parent "No. 5350" quite early in September. The resulting new variety blooms in mid-September, deriving its earliness of flowering from the seed parent "No. 5350."

The blooms of my new variety appear from about mid-September and profusely and continuously until a killing frost, and thus the blooming season is a relatively long period of time.

The foliage and plant habit of my new variety are improvements over both the parents in that the plant habit is more compact, somewhat branching and very vigorous, the foliage being much more abundant and of smooth texture.

My new variety has been asexually reproduced by cuttings, in the vicinity of Niles, Michigan.

My new variety has been found to retain its distinctive characteristics through successive asexual reproductions.

The accompanying drawing forming a part hereof shows a typical plant of my new variety of chrysanthemum.

The following is a detailed description of my new variety of chrysanthemum plant, the color references being to the Nickerson Color Fan published by Munsell Color Company:

Parentage: Seedling.
- *Seed parent.*—"No 5350" (unpatented).
- *Pollen parent.*—"Cupid" (unpatented).

Classification: Botanic—*Chrysanthemum indicum.*

*Flower*

Blooming habit: Blooms very profusely from early September and continuously until killing frost in the fall.

Bud:
- *Size.*—Large.
- *Form.*—Short with flat top. Not affected by hot or wet weather.
- *Color.*—When petals begin to unfurl—Munsell Hue 10P 7/7 moderate purplish pink washed with 10P 6/9 light reddish purple. When half blown: inside of petals—Munsell Hue 2.5RP 7/8 moderate purplish pink washed with 2.5RP 8/5 light purplish pink; reverse of petals—white washed with pale purplish pink 10P 8/5.
- *Peduncle.*—Long.
- *Aspect.*—Rough.
- *Color.*—Medium green.
- *Strength.*—Stiff; erect.
- *Opening.*—Bud opens well—somewhat affected by adverse conditions.

Bloom:
- *Size.*—Large. Average size when fully expanded—5 inches (disbudded).
- *Borne.*—In clusters; iregular.
- *Stems.*—Long.
- *Form.*—Flat. Permanence—retains its form to the end.
- *Petalage.*—Very double. Number of petals under normal conditions—innumerable.
- *Color.*—Center of flower—7.5YR 9/4 Munsell Hue 7.5YR. Outer petals—2.5R 9/3 Munsell Hue 2.5R. Base of petals (singlet)—2.5R 9/3 Munsell Hue 2.5R. Inside of petals—2.5R 9/3 Munsell Hue 2.5R. Reverse of petals—2.5R 9/3 Munsell Hue 2.5R. General tonality from a distance 2.5R 9/3 Munsell Hue 2.5R.
- *Discoloration.*—First week—retains same color. Second week—retains much the same color. Third week—retains much the same color.

Petals:
- *Texture.*—Thin. Bleaches in hot weather. Susceptible to fungus infection in wet weather.
- *Appearance.*—Inside—velvety. Outside—satiny.
- *Form.*—Pointed.
- *Arrangement.*—Imbricated.
- *Petaloids.*—None.
- *Persistance.*—Hang on and dry.
- *Lastingness.*—On the plant—very long. As cut flower—long.

Genital organs:

*Stamens, anthers.*—Small; few.

*Color.*—Yellow.

*Arrangement.*—Regular around styles.

*Stamens, filaments.*—Short.

*Color.*—White.

*Styles.*—Columnar.

*Length.*—Short.

*Stigmas.*—White.

*Ovaries.*—All enclosed in calyx.

Fruit: Variety is fertile with own pollen.

*Form.*—Oblong shaped.

*Aspect.*—Rough.

*Color at maturity.*—Brownish grey.

Form: Bush.

Growth: Vigorous; dwarf; branching; compact.

Foliage:

*Size.*—Large.

*Quantity.*—Abundant.

*Color.*—New foliage: upper side—normal green; under side—light green. Old foliage: upper side—dark green; under side—dark green.

*Shape.*—Three lobed.

*Texture.*—Upper side—smooth; flat. Under side—velvety. Ribs and veins—ordinary.

*Edge.*—Smooth.

*Leaf stem.*—Green in color. Under side—smooth.

*Stipules.*—Short.

*Disease resistance.*—Under certain conditions susceptible to mildew.

I claim:

A new and distinct variety of chrysanthemum plant substantially as herein disclosed, characterized as to novelty by the pale orange yellow center, pale pink general tonality, improved reflexed type bloom, very double arrangement of its petals, the earlier, continuous, long blooming period, its more vigorous, compact plant habit and larger, more abundant foliage.

No references cited.